US00PP11904P2

(12) United States Plant Patent
Glicenstein

(10) Patent No.: US PP11,904 P2
(45) Date of Patent: Jun. 5, 2001

(54) CHRYSANTHEMUM PLANT NAMED 'BRIGHT STEPHANIE'

(75) Inventor: Leon Glicenstein, State College, PA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/225,014

(22) Filed: Jan. 4, 1999

(51) Int. Cl.[7] ..... A01H 5/00

(52) U.S. Cl. ..... Plt./295

(58) Field of Search ..... Plt./295, 289

(56) References Cited

U.S. PATENT DOCUMENTS

P.P. 9,445 * 1/1996 VandenBerg ..... Plt./294
4,616,099 * 10/1986 Sparkes ..... 47/58

OTHER PUBLICATIONS

Broertjes, et al., 1980, A mutant of a mutant of a . . . Irradiation of progressive radiation –induced mutants in a mutation breeding programme with *Chrysanthemum morifolium*, Euphytica, 29:525–530.*
Gosling ed., 1979, "The Crysanthemum Manual —6$^{th}$ edition", The National Chrysanthemum Society, London, Essex Telegraph Press, Ltd., pp. 329–336.*
Broertjes, et al., 1978, "Application of Mutation Breeding Methods in the Improvement of Vegetatively Propagated Crops", Elsevier Sci. Pub. Co., New York, pp. 162–175.*
Searle, et al., 1968, "Chrysanthemums the Year Round", Blanford Press, London, pp. 27–29, 320–327.*
Chan, 1966, "Chrysanthemum and rose mutations induced by x–rays", Am. Soc. Hort. Sci. Proc. pp. 613–620.*
Broertjes, 1966, Mutation breeding of chrysanthemums, Euphytica, 15: 156–162.*
Dowrick, et al., 1966, "The induction of mutations in Chrysanthemum using X– and gamma radiation", Euphytica, 15:204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Bright Stephanie', characterized by its uniformly mounded plant habit; relatively early flowering; daisy-type inflorescences that are about 5.1 cm in diameter; attractive bright yellow ray florets and darker yellow disc florets; and numerous inflorescences per plant.

1 Drawing Sheet

BACKGROUND OF THE INVENTION

The present invention relates to a new and distinct cultivar of Chrysanthemum plant, botanically known as *Dendranthema grandiflora* and referred to by the cultivar name Bright Stephanie.

The new cultivar is a product of a mutation induction breeding program conducted by the inventor in Fort Myers, Fla., and Salinas, Calif. The objective of the breeding program is to create new garden-type Chrysanthemum cultivars having with desirable inflorescence form and color and good garden performance.

The new cultivar originated by exposing unrooted cuttings of the Chrysanthemum cultivar Stephanie (disclosed in U.S. Plant Pat. No. 9,445) to X-ray radiation at a level of 2,000 rads in Jun. 1994. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The cultivar Bright Stephanie was discovered and selected by the inventor as a single flowering plant within this population in December, 1994. The selection of this plant was based on its desirable ray floret color.

Asexual reproduction of the new cultivar by terminal cuttings taken in a controlled environment in Salinas, Calif., has shown that the unigue features of this new Chrysanthemum are stable and reproduced true to type in successive generations.

SUMMARY OF THE INVENTION

The cultivar Bright Stephanie has not been observed under all possible environmental conditions. The phenotype may vary somewhat with variations in environment such as temperature, daylength and light intensity, without, however, any variance in genotype.

The following traits have been repeatly observed and are determined to be the unique characteristics of 'Bright Stephanie'. These characteristics in combination distinguish 'Bright Stephanie' as a new and distinct cultivar:

1. Uniformly mounded plant habit.

2. Relatively early flowering.

3. Daisy-type inflorescences that are about 5.1 cm in diameter.

4. Attractive bright yellow ray florets and darker yellow disc florets.

5. Numerous inflorescences per plant.

The new Chrysanthemum is similar to the parent cultivar Stephanie. However in side-by-side comparisons under commercial practice, plants of the new Chrysanthemum differed from plants of the cultivar Stephanie in the following characteristics:

1. Plants of the new Chrysanthemum do not flower as uniformly as plants of the cultivar Stephanie.

2. Plants of the new Chrysanthemum have bright yellow ray florets and darker yellow disc florets whereas plants of the cultivar Stephanie have white ray florets and golden yellow disc florets.

3. Plants of the new Chrysanthemum are more compact than plants of the cultivar Stephanie.

4. Plants of the new Chrysanthemum flower earlier than plants of the cultivar Stephanie.

5. Ray floret color of plants of the new Chrysanthemum fades more than ray floret color of plants of the cultivar Stephanie.

BRIEF DESCRIPTION OF THE PHOTOGRAPH

The accompanying photograph illustrates the overall appearance of the cultivar. The photograph comprises a top perspective view of a typical flowering plant of 'Bright Stephanie'. This photograph shows the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, under conditions which approximate those generally used in commerical garden Chrysanthemum production. One rooted cutting was planted in a 15-cm container on Jul. 20, 1998 and plants were grown outdoors under natural season conditions. Measurements and numerical values represent averages for typical flowering containers.

Botanical classification: *Dendranthema grandiflora* cultivar Bright Stephanie.

Commercial classification: Daisy-type garden chrysanthemum.

Parentage: Induced mutation of *Dendranthema grandifora* cultivar Stephanie, disclosed in U.S. Plant Pat. No. 9,445.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy-type garden Chrysanthemum. Inverted triangle. Stems initially upright, then outwardly spreading giving a uniformly mounded appearance to the plant. Freely branching with lateral branches potentially developing at every node, when pinched, about 11 laterals develop.

*Plant height.*—About 24 cm.

*Plant spread.*—About 31 cm.

*Foliage description.*—Leaf arrangement: Alternate. Length: About 4.25 cm. Width: About 3.7 cm. Apex: Cuspidate. Base: Attenuate. Margin: Palmately lobed, sinuses typically parallel. Texture: Upper surface sparsely pubescent; lower surface moderately pubescent. Veins prominent on lower surface. Petiole length: About 1.3 cm. Petiole diameter: About 2 mm. Color: Young foliage upper surface: 147A. Young foliage lower surface: 147B. Mature foliage upper surface: 147A. Mature foliage lower surface: 147B. Venation upper surface: 147A/147B. Venation lower surface: 147B.

Inflorescence description:

*Appearance.*—Daisy-type inflorescence form with elongated oblong-shaped ray florets that are concave and give the appearance of being somewhat quilled. Inflorescences borne on terminals above foliage, arising from leaf axils. Disk and ray florets arranged acropetally on a capitulum. One inflorescence per terminal with numerous inflorescences per plant, about 10 per lateral stem.

*Flowering response.*—Under natural season conditions, plants flower in early September in the Northern Hemisphere, about 61 days after planting, and flower for at least three weeks depending on weather conditions.

*Inflorescence bud:* (*before showing color*).—Height: About 5 mm. Diameter: About 9 mm. Phyllary color: Darker than 143A.

*Inflorescence size.*—Diameter: About 5.1 cm. Depth (height): About 1.8 cm. Diameter of disc: About 1.2 cm.

*Ray florets.*—Shape: Elongated oblong-shaped ray florets that are concave and give the appearance of being somewhat quilled. Length: About 2.4 cm. Width: About 3 mm. Apex: Rounded. Margin: Entire. Texture: Smooth, glabrous. Orientation: Mostly upright to horizontal, 135 to 90° to the peduncle. Number of ray florets per inflorescence: About 81 in several rows. Color: When opening: 6A. Opened inflorescence: Upper surface: 6A. Lower surface: 6D.

*Disc florets.*—Shape: Tubular, apex dentate. Length: About 6 mm. Width: Apex: About 2 mm. Base: About 1 mm. Number of disc florets per inflorescence: Typically more than 100. Color: Immature: 154A. Mature: Apex 12A. Mid-section and base: White.

*Peduncle.*—Aspect: Flexible, angled about 35° to the stem. Length: First peduncle: About 6.8 cm. Fourth peduncle: About 10.3 cm. Diameter: About 2 mm. Texture: Pubescent. Color: 147B.

*Reproductive organs.*—Androecium: Present on disc florets only. Anther color: Light yellow. Pollen: Scarce. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Bright Stephanie', as illustrated and described.

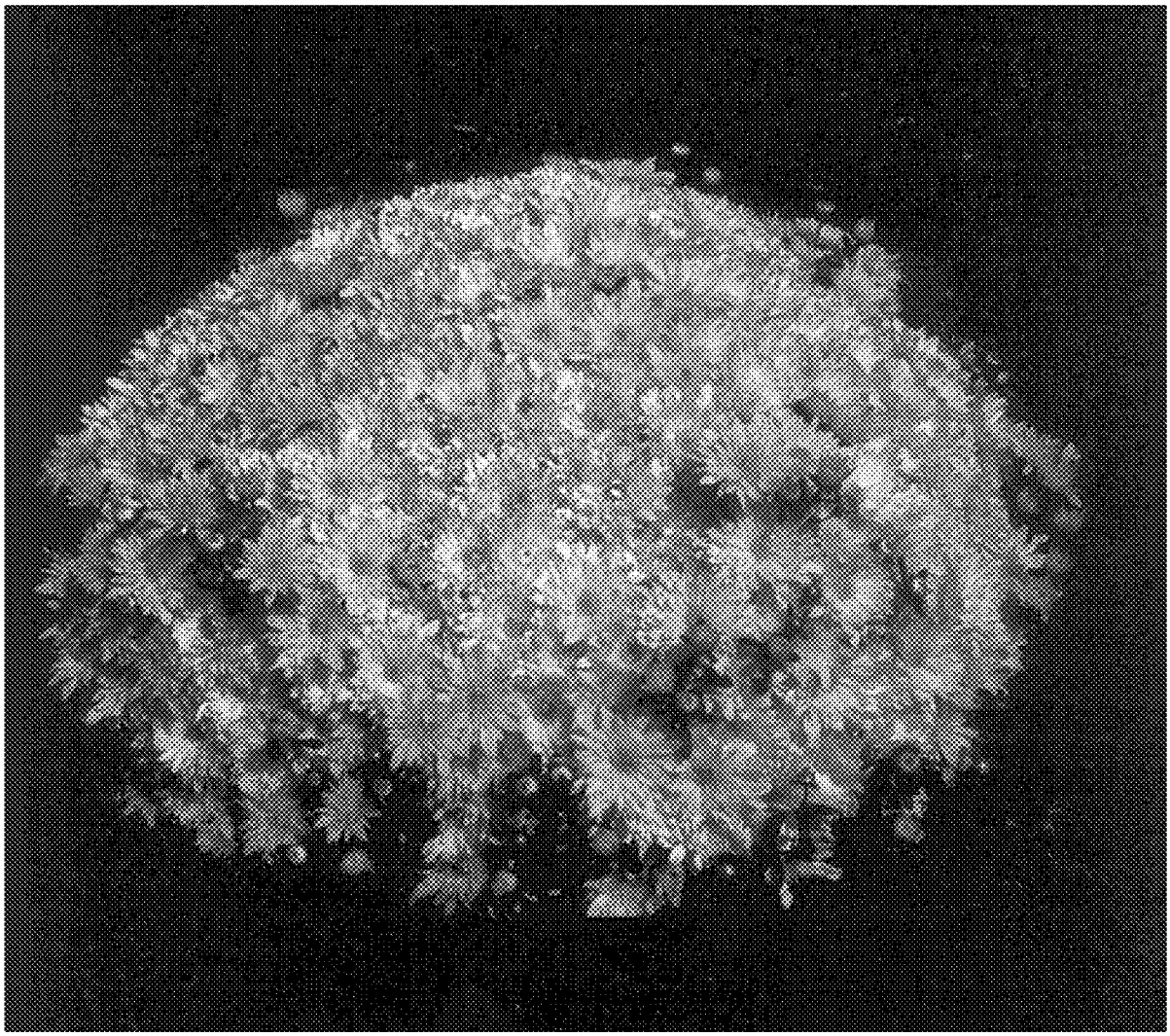

* * * * *